(12) United States Patent
Simon et al.

(10) Patent No.: US 8,209,034 B2
(45) Date of Patent: *Jun. 26, 2012

(54) METHODS AND APPARATUS FOR ELECTRICAL STIMULATION TREATMENT USING ESOPHAGEAL BALLOON AND ELECTRODE

(75) Inventors: Bruce Simon, Mountain Lakes, NJ (US); Steven Mendez, Chester, NJ (US); Hecheng Hu, Cedar Grove, NJ (US); Richard P. Dickerson, Rockaway, NJ (US); James R. Pastena, Succasunna, NJ (US)

(73) Assignee: ElectroCore LLC, Morris Plains, NJ (US)

( * ) Notice: Subject to any disclaimer, the term of this patent is extended or adjusted under 35 U.S.C. 154(b) by 859 days.

This patent is subject to a terminal disclaimer.

(21) Appl. No.: 12/338,191

(22) Filed: Dec. 18, 2008

(65) Prior Publication Data

US 2010/0160996 A1   Jun. 24, 2010

(51) Int. Cl.
*A61N 1/00* (2006.01)
(52) U.S. Cl. ...................................... 607/124
(58) Field of Classification Search .................. 607/124, 607/116; 600/41, 547; 128/898
See application file for complete search history.

(56) References Cited

U.S. PATENT DOCUMENTS

| | | | |
|---|---|---|---|
| 4,198,936 | A | 4/1980 | Pagel et al. |
| 4,304,239 | A | 12/1981 | Perlin |
| 4,351,330 | A | 9/1982 | Scarberry |
| 4,574,807 | A | 3/1986 | Hewson et al. |
| 4,640,298 | A | 2/1987 | Pless et al. |
| 4,706,688 | A | 11/1987 | Don Michael et al. |
| 4,817,611 | A | 4/1989 | Arzbaecher et al. |
| 4,919,147 | A | 4/1990 | Reinhardt et al. |
| 5,003,991 | A | 4/1991 | Takayama et al. |
| 5,056,532 | A | 10/1991 | Hull et al. |
| 5,249,585 | A | 10/1993 | Turner et al. |
| 5,366,490 | A | 11/1994 | Edwards et al. |
| 5,370,675 | A | 12/1994 | Edwards et al. |
| 5,370,679 | A | 12/1994 | Atlee, III |

(Continued)

FOREIGN PATENT DOCUMENTS

EP   0970718 A2   1/2000
(Continued)

OTHER PUBLICATIONS

Supplementary European Search Report Application No. EP09730047, Dec. 19, 2011 of corresponding EP patent application.

(Continued)

*Primary Examiner* — George Manuel
*Assistant Examiner* — Robert Wieland
(74) *Attorney, Agent, or Firm* — John T. Raffle (57) ABSTRACT

Methods and apparatus for treating ailments provide for: inserting a balloon-electrode device into an esophagus of a mammal, the balloon-electrode device including: (i) a nasogastral (NG) having an internal passageway and an external surface, (ii) at least one electrode coupled to the external surface of the NG tube, (iii) a conductor extending through the internal passageway of the NG tube and electrically connecting to the electrode, and (iv) a balloon surrounding the electrode and a portion of the NG tube; inflating the balloon with fluid such that the electrode is substantially centrally located within an interior volume of the balloon; and applying at least one electrical signal to the electrode via the conductor such that an electro-magnetic field emanates from the electrode to at least one of nerves and muscles of the mammal.

41 Claims, 6 Drawing Sheets

U.S. PATENT DOCUMENTS

| | | | |
|---|---|---|---|
| 5,431,696 A | 7/1995 | Atlee, III | |
| 5,540,730 A | 7/1996 | Terry, Jr. et al. | |
| 5,626,618 A | 5/1997 | Ward et al. | |
| 5,692,506 A | 12/1997 | Linder | |
| 5,707,400 A | 1/1998 | Terry, Jr. et al. | |
| 5,800,378 A | 9/1998 | Edwards et al. | |
| 5,967,977 A | 10/1999 | Mullis et al. | |
| 6,006,138 A | 12/1999 | Don Michael | |
| 6,083,249 A | 7/2000 | Familoni | |
| 6,083,255 A | 7/2000 | Laufer et al. | |
| 6,148,222 A | 11/2000 | Ramsey, III | |
| 6,198,970 B1 | 3/2001 | Freed et al. | |
| 6,327,503 B1 | 12/2001 | Familoni | |
| 6,341,236 B1 | 1/2002 | Osorio et al. | |
| 6,347,247 B1 | 2/2002 | Dev et al. | |
| 6,356,786 B1 | 3/2002 | Rezai et al. | |
| 6,356,787 B1 | 3/2002 | Rezai et al. | |
| 6,366,814 B1 | 4/2002 | Boveja et al. | |
| 6,423,058 B1 | 7/2002 | Edwards et al. | |
| 6,425,877 B1 | 7/2002 | Edwards | |
| 6,438,423 B1 | 8/2002 | Rezai et al. | |
| 6,475,213 B1 | 11/2002 | Whayne et al. | |
| 6,609,030 B1 | 8/2003 | Rezai et al. | |
| 6,610,713 B2 | 8/2003 | Tracey | |
| 6,656,960 B2 | 12/2003 | Puskas | |
| 6,778,854 B2 | 8/2004 | Puskas | |
| 6,819,956 B2 | 11/2004 | DiLorenzo | |
| 6,865,416 B2 | 3/2005 | Dev et al. | |
| 6,871,092 B2 | 3/2005 | Piccone | |
| 6,885,888 B2 | 4/2005 | Rezai | |
| 6,934,583 B2 | 8/2005 | Weinberg et al. | |
| 6,937,896 B1 | 8/2005 | Kroll | |
| 6,955,173 B2 | 10/2005 | Lesh | |
| 6,980,865 B1 | 12/2005 | Wang et al. | |
| 7,008,419 B2 | 3/2006 | Shadduck | |
| 7,043,307 B1 | 5/2006 | Zelickson et al. | |
| 7,072,720 B2 | 7/2006 | Puskas | |
| 7,142,910 B2 | 11/2006 | Puskas | |
| 7,167,750 B2 | 1/2007 | Knudson et al. | |
| 7,229,469 B1 | 6/2007 | Witzel et al. | |
| 7,292,890 B2 | 11/2007 | Whitehurst et al. | |
| 7,310,552 B2 | 12/2007 | Puskas | |
| 7,326,207 B2 | 2/2008 | Edwards | |
| 7,400,929 B2 | 7/2008 | Zelickson et al. | |
| 7,840,278 B1 * | 11/2010 | Puskas | 607/116 |
| 2001/0031941 A1 | 10/2001 | Edwards et al. | |
| 2002/0010495 A1 | 1/2002 | Freed et al. | |
| 2002/0016344 A1 | 2/2002 | Tracey | |
| 2002/0016615 A1 | 2/2002 | Dev | |
| 2002/0116030 A1 | 8/2002 | Rezai | |
| 2002/0183682 A1 | 12/2002 | Darvish et al. | |
| 2002/0188289 A1 * | 12/2002 | Hegde | 606/41 |
| 2002/0198570 A1 | 12/2002 | Puskas | |
| 2003/0009208 A1 | 1/2003 | Snyder et al. | |
| 2003/0074039 A1 | 4/2003 | Puskas | |
| 2003/0195593 A1 | 10/2003 | Ingle et al. | |
| 2004/0039431 A1 | 2/2004 | Machold et al. | |
| 2004/0059383 A1 | 3/2004 | Puskas | |
| 2004/0172075 A1 | 9/2004 | Shafer et al. | |
| 2004/0215235 A1 | 10/2004 | Jackson et al. | |
| 2004/0249416 A1 | 12/2004 | Yun et al. | |
| 2005/0021092 A1 | 1/2005 | Yun et al. | |
| 2005/0065553 A1 | 3/2005 | Ben Ezra et al. | |
| 2005/0065562 A1 | 3/2005 | Rezai | |
| 2005/0065573 A1 | 3/2005 | Rezai | |
| 2005/0075701 A1 | 4/2005 | Shafer | |
| 2005/0075702 A1 | 4/2005 | Shafer | |
| 2005/0125044 A1 | 6/2005 | Tracey | |
| 2005/0149146 A1 | 7/2005 | Boveja et al. | |
| 2005/0153885 A1 | 7/2005 | Yun | |
| 2005/0165388 A1 | 7/2005 | Bhola | |
| 2005/0182463 A1 | 8/2005 | Hunter et al. | |
| 2005/0216062 A1 | 9/2005 | Herbst | |
| 2005/0240241 A1 | 10/2005 | Yun | |
| 2005/0256028 A1 | 11/2005 | Yun | |
| 2005/0273146 A1 | 12/2005 | DeSimone et al. | |
| 2006/0129215 A1 | 6/2006 | Helmus et al. | |
| 2006/0135998 A1 | 6/2006 | Libbus et al. | |
| 2006/0167498 A1 | 7/2006 | DiLorenzo | |
| 2006/0259107 A1 | 11/2006 | Caparso et al. | |
| 2007/0106337 A1 | 5/2007 | Errico et al. | |
| 2007/0106338 A1 | 5/2007 | Errico | |
| 2007/0106339 A1 | 5/2007 | Errico et al. | |
| 2007/0191902 A1 | 8/2007 | Errico et al. | |
| 2007/0213645 A1 | 9/2007 | Zumeris et al. | |
| 2007/0225768 A1 | 9/2007 | Dubak | |
| 2008/0039904 A1 | 2/2008 | Bulkes et al. | |
| 2010/0010368 A1 * | 1/2010 | Kassab | 600/547 |

FOREIGN PATENT DOCUMENTS

| | | |
|---|---|---|
| WO | WO 2006/060458 A1 | 6/2006 |

OTHER PUBLICATIONS

International Search Report and Written Opinion for Corresponding PCT Application PCT/US09/36259, May 11, 2009.

* cited by examiner

FIG. 7B

METHODS AND APPARATUS FOR ELECTRICAL STIMULATION TREATMENT USING ESOPHAGEAL BALLOON AND ELECTRODE

BACKGROUND OF THE INVENTION

The present invention relates to the delivery of electromagnetic impulses (and/or fields) to bodily tissues for therapeutic purposes, and more specifically to devices and methods for treating conditions through delivery of the electromagnetic impulses using an esophageal balloon and electrode device.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

One of the most successful modern applications of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Among the developments in the treatment of patients with heart ailments has been the introduction of electrodes for electrical stimulation through the esophagus. For example, esophageal stimulation and monitoring leads are known in the art, adapted specifically for cardiac pacing, as disclosed in U.S. Pat. Nos. 4,574,807; 4,198,936; and 4,706,688, the entire disclosures of which are hereby incorporated by reference herein. Typically, esophageal pacing leads include one or more balloons, adapted to stabilize the location of the lead in the esophagus. In some cases, the electrodes are located on the balloon, as in U.S. Pat. No. 4,198,936. In other cases, the electrodes are located proximal or distal to the balloon as in U.S. Pat. No. 4,574,807. In some other cases, the balloon is arranged eccentrically, and is used both to stabilize the lead and urge the electrodes into contact with the anterior inner surface of the esophagus, as in U.S. Pat. No. 4,706,688.

More specifically, U.S. Pat. No. 4,706,688 discloses a device 10 inserted into the esophagus 34 of a patient. The device 10 is inserted through the nasal region 32, through the esophagus 34 and into the stomach 36. Once the device 10 has been inserted, fluid is caused to flow along airway 24 such that a balloon cuff 18 expands. The purpose of cuff 18 is to locate the gastroesophageal junction just proximate to the cuff 18. A second balloon cuff 20 is located posterior to the heart region 40 such that when it is expanded, at least some of the electrodes 26 abut against the esophagus 34 adjacent the heart 40.

U.S. Pat. No. 5,056,532 discloses a lead having an elongated flexible lead body 10, which is provided with three longitudinal lumens. At the distal end of the lead a balloon 12 is mounted around the external surface of the lead body 10. Proximal to balloon 12 is a second balloon 20. An electrode lead 24 is slideably mounted within a lumen within lead body 10, and ventricular electrodes 26 and 28 are mounted to lead 24. The electrode lead 24 and electrodes 26 and 28 may be slideably adjusted relative to the position of balloon 20. A third balloon 30 is located proximal to balloon 20. Atrial electrodes 34 and 36 are located on electrode lead 24, such that movement of lead 24 within the lead body 10 adjusts the positions of electrodes 34 and 36 relative to balloon 30.

The lead is advanced through the mouth or the nasal cavity, down the esophagus until the distal end 18 of the lead is well within the stomach. The balloon 12 is then inflated, and the lead is withdrawn until balloon 12 lies against the gastroesophageal junction. Balloons 20 and 30 are then inflated, urging electrode lead 24 against the anterior inner surface of the esophagus, closest to the heart. Notably, when the balloons 20 and 30 are inflated, electrodes 26 and 28 and electrodes 34 and 36 are urged into contact with the anterior inner surface of the esophagus.

It has been discovered that the above esophageal electrode and balloon configurations are not satisfactory for all applications. Accordingly, there is a need in the art for new products and methods for treating conditions through delivery of electromagnetic impulses using esophageal balloon electrodes.

SUMMARY OF THE INVENTION

One or more embodiments of the present invention involve products and methods of treatment of bronchoconstriction and/or bronchospasm associated with asthma, anaphylaxis, and/or other pathologies involving the constriction of the primary airways. Other treatments may include one or more of hypotension, epilepsy, depression, obesity, and any other ailment affected by vagus nerve transmissions. The products and methods utilize delivering electromagnetic fields that may be applied to the anatomy of the patient (such as to the vagus nerve) via an esophageal electrode/balloon device to temporarily block and/or modulate signals associated with constriction of the smooth muscle of the patient's bronchia.

The smooth muscles that line the bronchial passages are controlled by a confluence of vagus and sympathetic nerve fiber plexuses. Spasms of the bronchi during asthma attacks and anaphylactic shock can often be directly related to pathological signaling within these plexuses. Anaphylactic shock and asthma are major health concerns.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release of the molecules that mediate the inflammatory process. The second strategy is to provide a smooth muscle relaxant (an anticholinergic and/or anti-adrenergic medication) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Anaphylaxis ranks among the other airway occluding disorders of this type as the most deadly, claiming more than eight thousand deaths per year in the United States alone. Anaphylaxis (the most severe form of which is anaphylactic shock) is a severe and rapid systemic allergic reaction to an allergan. Minute amounts of allergans may cause a life-threatening anaphylactic reaction. Anaphylaxis may occur after ingestion, inhalation, skin contact or injection of an allergan. Anaphylactic shock usually results in death in minutes if untreated. Anaphylactic shock is a life-threatening medical emergency because of rapid constriction of the airway. Brain damage sets in quickly without oxygen. Anaphylactic shock itself accounts for approximately 1,500 deaths every year in the United States.

The triggers for these fatal reactions range from foods (nuts and shellfish), to insect stings (bees), to medication (radiocontrasts and antibiotics). It is estimated 1.3 to 13 million people in the United States are allergic to venom associated with insect bites; 27 million are allergic to antibiotics; and 5-8 million suffer food allergies. All of these individuals are at risk of anaphylactic shock from exposure to any of the foregoing allergens. In addition, anaphylactic shock can be brought on by exercise. Yet all are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

In accordance with one or more embodiments of the present invention, devices and methods for the treatment of one or more ailments may include: a nasogastral (NG) tube having an internal passageway and an external surface; at least one electrode coupled to the external surface of the NG tube; a conductor extending through the internal passageway of the NG tube and electrically connecting to the electrode; and a balloon surrounding the electrode and a portion of the NG tube such that when the balloon is inflated with fluid, the electrode is substantially centrally located within an interior volume of the balloon.

The device may further include an electrical signal generator operating to apply at least one electrical signal to the conductor such that, when the inflated balloon and electrode combination is positioned in an esophagus of a mammal, an electromagnetic field emanates from the electrode to the anatomy of the mammal, such as to the vagus nerve. In accordance with one embodiment, the at least one electrical signal, in combination with electrical characteristics of the electrode, the fluid, and the material of the balloon, may be such that at least one of: (i) a magnitude of constriction of bronchial smooth muscle of the mammal is reduced, (ii) a blood pressure of the mammal is either reduced or increased, (iii) epilepsy, (iv) depression, (v) obesity, and (vi) any other ailment affected by vagus nerve transmissions.

The device may also include a return electrode, which when applied to the mammal, the electromagnetic field emanating from the electrode is a substantially radial pattern.

The balloon may be sized and shaped such that it operates to: (i) slide, in a deflated state, past a cricoid cartilage of the mammal, and (ii) seat, when in an inflated state, when slid back toward the cricoid cartilage.

Preferably, electrical properties of the electrode, the fluid, and the material of the balloon are such that a resistance through the electrode, the fluid, and the material of the balloon is no more than about 200 Ohms.

The electrical signal generator preferably operates such that the at least one electrical signal is of a frequency between about 1 Hz to 3000 Hz, a pulse duration of between about 10-1000 us, and an amplitude of between about 1-20 volts. The at least one electrical signal may be one or more of: a full or partial sinusoid, a square wave, a rectangular wave, and triangle wave. By way of example, the at least one electrical signal may be of a frequency between about 15 Hz to 35 Hz. Alternatively, the at least one electrical signal may be of a frequency of about 25 Hz. By way of example, the at least one electrical signal may have a pulsed on-time of between about 50 to 1000 microseconds, such as between about 100 to 300 microseconds, or about 200 microseconds. By way of example, the at least one electrical signal may have an amplitude of about 5-15 volts, such as about 12 volts.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise arrangements and instrumentalities shown.

DETAILED DESCRIPTION OF THE PREFERRED EMBODIMENTS

Figure 1A:
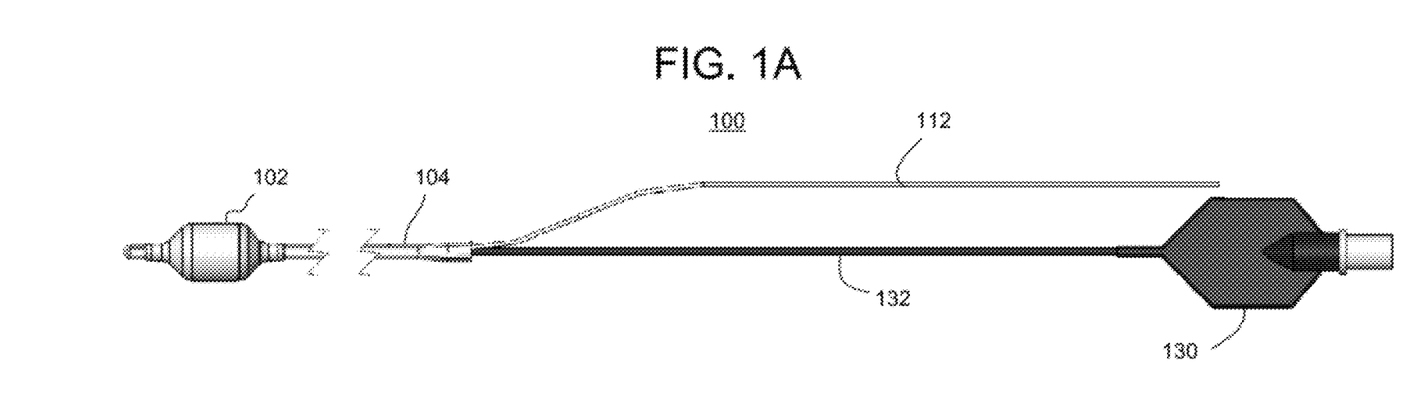
FIG. 1A is a schematic view of an esophageal electrode device in accordance with one or more aspects of the present invention.
Figure 1B:
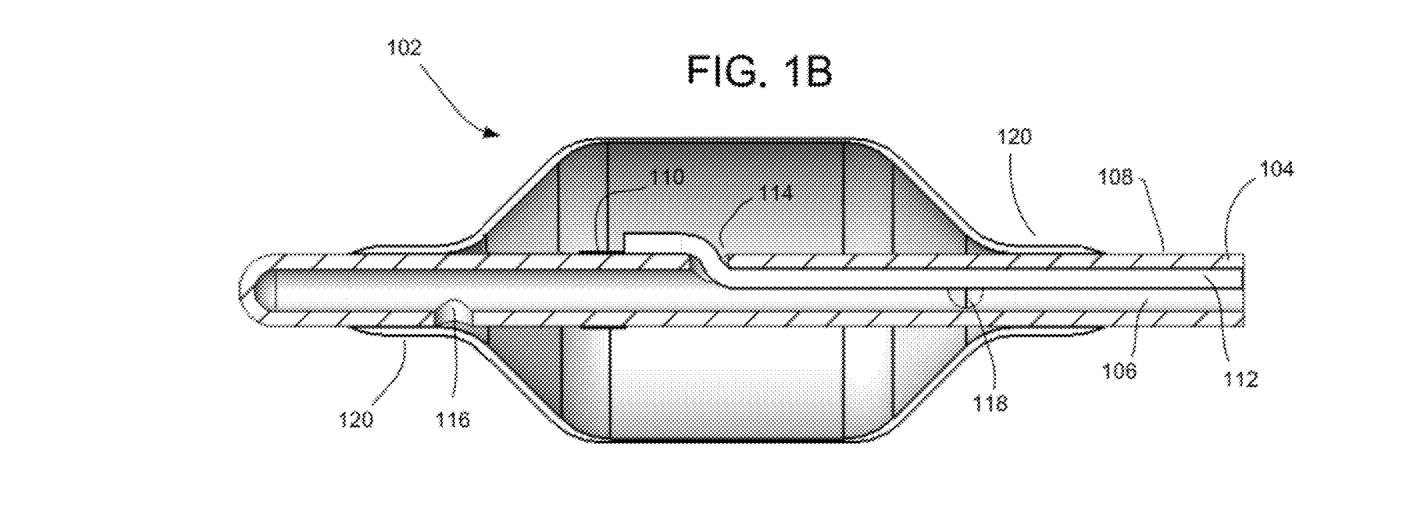
FIG. 1B is a cross-sectional view taken through the balloon of the esophageal electrode device of FIG. 1A.

With reference to FIGS. 1A, 1B, an electromagnetic field producing device 100 may be utilized in delivering an electromagnetic field to a patient. In particular, the device 100 is designed to be introduced into the esophagus of the patient and located therein at a position that (when activated) achieves a therapeutic result. The device 100 includes an inflatable balloon 102 and a catheter, or nasogastral (NG) tube 104, sized and shaped (when the balloon 102 is deflated) to slide into the patient's esophagus.

By way of example, the balloon 102 may preferably be formed from an ion-permeable, soft, flexible, and/or distensible material with a thickness of about 0.001 inches. The balloon preferably has a length of between about 1-3 cm (such as 2 cm), a diameter of between about 1.5-4.0 cm (such as 2-3 cm), and a fluid pressure therein of between about 1-3 pounds per square inch (such as 2 psi) when inflated. Obviously, under the stresses experienced during insertion, extraction and inflation, the balloon 102 should not separate from the NG tube 104, tear or leak. The NG tube 104 may be of a standard type formed out of polyurethane, measuring about 36 cm long, and having inside and outside diameters of 1.6 mm and 2.5 mm, respectively (although other lengths, diameters, and materials may be employed). In order to assist in the placement of the balloon 102 at a desired location within the esophagus, the NG tube 104 may include markers along its length, such as one marker about every 1 cm.

With reference to FIG. 1B, the NG tube 104 includes an internal passageway 106 and an external surface 108. At least one electrode 110 is coupled to the external surface 108 of the NG tube 104 (such as by a UV curable adhesive, such as Dymax 204-CTH). By way of example, the at least one electrode 110 may be of a general cylindrical shape and may extend around the external surface 108 of the NG tube 104. Although there are a number of sizes and shapes that would suffice to implement the electrode 110, by way of example, the at least one electrode 110 may be between about 1.0-1.5 mm long (such as 1.27 mm), may have an outside diameter of between about 2.6-2.85 mm (such as 2.77 mm), and may have an inside diameter of between about 2.5-2.75 mm (such as 2.67 mm) A suitable electrode 110 may be formed from Pt—IR (90%/10%).

A conductor 112 extends through the internal passageway 106 of the NG tube 104 and electrically connects to the electrode 110. By way of example, the conductor 112 may be a solid silver wire of about 0.25 mm diameter insulated with a PTFE material of about 0.33 mm diameter. The diameter of the insulating material of the conductor 112 should be less than the internal diameter of the NG tube 104 such that fluid may freely flow therein despite the presence of the conductor 112. The conductor 112 may be laser welded to the electrode 110 using known procedures.

Figure 2A:
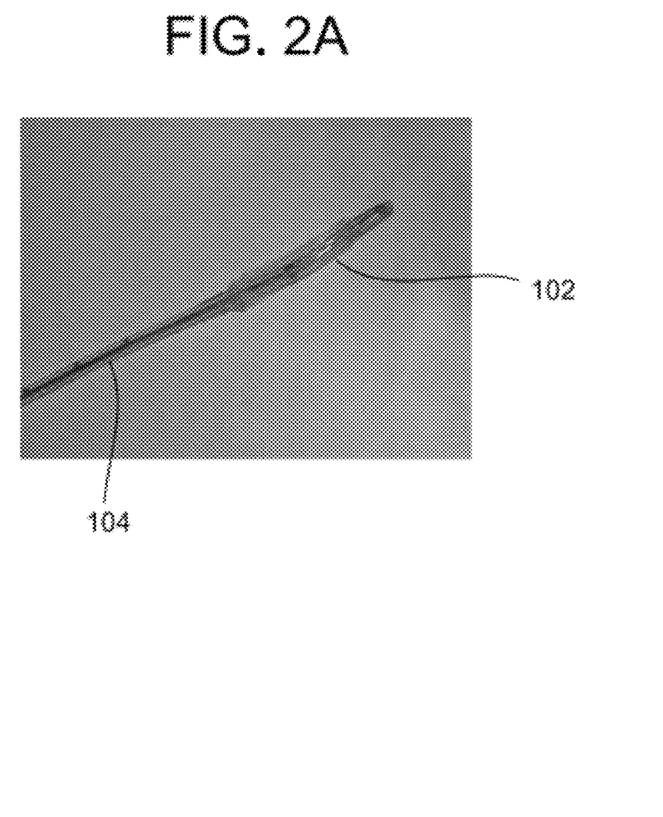
FIG. 2A is an illustration of a deflated balloon of the esophageal electrode device of FIG. 1A.
Figure 2B:
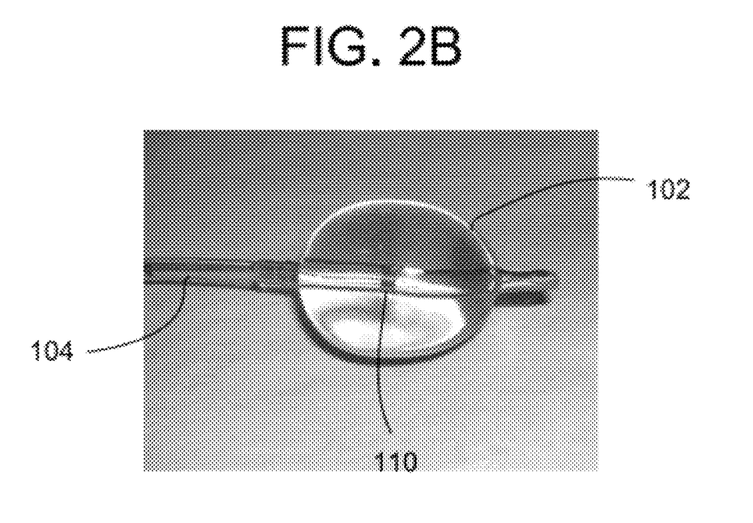
FIG. 2B is an illustration of an inflated balloon of the esophageal electrode device of FIG. 2A.

FIG. 1B is a schematic illustration of the balloon 102 in an inflated state, while FIG. 2B is a reproduction of a photograph illustrating a prototype of the device 100 with the balloon 102 inflated. FIG. 2A is a reproduction of a photograph illustrating the prototype of the device 100 with the balloon 102 deflated. A fluid, preferably a saline solution, passes into the balloon 102 through the NG tube 104 to inflate same. The balloon 102 is sized, shaped and located about the electrode 110 and a portion of the NG tube 104 such that when the balloon is inflated with fluid, the electrode 110 is substantially centrally located within an interior volume of the balloon 102. This configuration has several advantages over conventional electrode configurations, such as: (i) the metal of the electrode 110 is not too close to, and never comes in contact with, the patient's tissue, which means that there is no concern about tissue necrosis or excessive electric fields in the tissue; (ii) the electrode 110 may be used with direct current signal sources since any Faradic Products (e.g. $OH^-$, $H_2O_2$) would not reach excessively high concentrations at the tissue site; (iii) as the balloon 102 is filled with saline, the surface of the balloon 102 wets and permits good contact with the surrounding tissue of the patient, which may otherwise be dry; and (iv) the material of the balloon 102 is preferably very soft and flexible such that it gently conforms to the surrounding tissue of the esophagus.

To inflate the balloon 102, a number of features are provided with the device 100. A pilot balloon assembly 130, which may be of a standard type, is located at a proximal end of the device 100. The pilot balloon assembly 130 is in fluid communication with the NG tube 104 via fluid tube 132. The fluid tube 132 may enter the NG tube 104 along with the conductor 112, and the entry point may be sealed with an adhesive, such as Dymax 204-CTH UV curable adhesive. The pilot balloon assembly 130 includes a spring loaded valve that opens when introducing fluid into the pilot and the fluid tube 132, and/or when removing fluid therefrom.

The NG tube 104 may include a first aperture 114 through which the conductor 112 passes from the internal passageway 106 to the at least one electrode 110. The NG tube 104 may include second and third apertures 116, 118 extending from the internal passageway 106 to the external surface 108, and through which fluid may pass to inflate and deflate the balloon 102 (as will be discussed in more detail later herein). Preferably, the second and third apertures 116, 118 are disposed at proximal and distal ends 120, 122 of the balloon 102, respectively, and the first aperture 114 is located between the second and third apertures 116, 118.

The inflation process preferably includes a priming phase followed by an inflation phase. The priming phase preferably takes place prior to introducing the device 100 into the patient's esophagus. In the priming phase, a source of fluid, such as saline, is coupled to the pilot balloon assembly 130. The source of fluid may be a fluid filled syringe or the like. With the balloon 102 in a generally vertical orientation (with distal end 120 up), fluid is preferably introduced into the pilot, the fluid tube 132, the NG tube 104 and the balloon 102 via the syringe. The fluid will enter the balloon 102 mostly via the second and third apertures 116, 118. Air will tend to collect at the distal end 120 of the balloon 102 as the fluid enters the device and urges the air in that direction. Again, keeping the balloon upright, at least some of the fluid is drawn out of the balloon 102 by reversing the fluid flow at the pilot balloon assembly 130 and source of fluid. This reversal of fluid flow will create a vacuum and draw all the air out of the balloon 102 via the second aperture 116. Of course, there may be other ways to prime the device 100, however, the above approach is believed to be suitable.

After the device 100 is inserted into the patient's esophagus (preferably through the nasal passage), the inflation phase begins. The inflation phase includes causing the fluid to flow into the device 100 from the source (e.g., the syringe) until a desired balloon size and/or pressure is reached, such as the aforementioned 1-3 cm length, 1.5-4.0 cm diameter, and/or 1-3 psi pressure.

The electrical properties of the electrode 110, the fluid, and the material of the balloon 102 are preferably designed such that a resistance therethrough is no more than about 200 Ohms. More precisely, the impedance through the electrode 110, the fluid, and the material of the balloon 102 should be no more than about 200 Ohms at 1000 Hz. The electrical properties of the fluid may be as important as those of the electrode 110 in this regard. A fluid of about 5% saline solution is believed to work well, although modifications to the concentration and the chemical make-up of the fluid may be modified through simple experimentation by skilled artisans.

As noted above, the material of the balloon 102 is preferably ion-permeable so that when the balloon 102 is filled with saline, the surface of the balloon 102 wets. Preferably, when filled with 10 cc of saline, the flux of saline out of the balloon 102 (into a similar saline solution) should not exceed about 1 cc per hour. Lubrizol Tecophilic HP93A-100 is a material with these properties.

In an alternative embodiment, the electrode 110 may be implemented via the fluid itself within the balloon 102. Although a 5% saline solution would have a relatively high resistance compared to a metal electrode 110 implementation, those skilled in the art would appreciate that higher conductivity fluid solutions may be employed for such purposes. Additionally or alternatively, the conductor 112 may be implemented using the conductive fluid used to fill the balloon 102; indeed, such fluid is within the passage 106 anyway. Again, relatively high conductivity fluid would be desirable.

Figure 3:
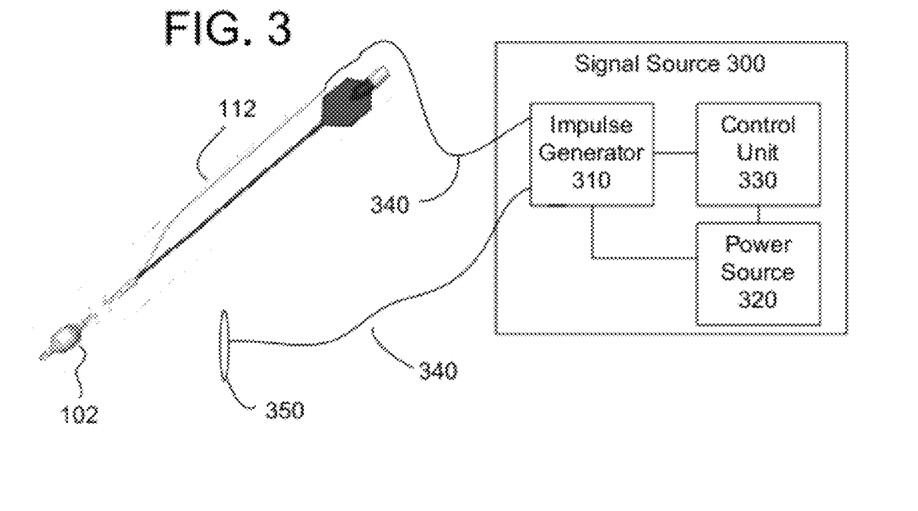
FIG. 3 is a schematic diagram of an electrical signal generating system for use with the esophageal electrode device of FIG. 1A.

With reference to FIG. 3, a complete system for using the device 100 includes an electrical signal generator (or source) 300. Source 300 operates to apply at least one electrical signal to the conductor 112 (via lead 340) such that, when the inflated balloon 102 (and electrode 110) is positioned in the esophagus of a patient, an electromagnetic field emanates from the electrode 110 to the anatomy of the mammal in the vicinity of the esophagus to achieve a therapeutic result.

Unlike some known techniques, which target a specific location of the patient's anatomy, such as a very specific location of a nerve, the return electrode 350 placement is preferably such that when applied to the mammal, the electromagnetic field emanating from the electrode 110 is a substantially radial pattern—in other words, the pattern of the electromagnetic field emanating from the electrode 110 is not focused on any particular point, or small, localized region of the patient's anatomy. This is preferably achieved by applying the return electrode 350 to an external portion of the patient, such as to at least one of the upper-back, the chest, and/or the stomach.

The source 300 may be tailored for the treatment of a particular ailment and may include an electrical impulse generator 310, a power source 320 coupled to the electrical impulse generator 310, and a control unit 330 in communication with the electrical impulse generator 310 and the power source 320. Electrodes 340 provide source and return paths for the at least one electrical signal to/from the electrode 110 and return electrode 350.

The control unit 330 may control the electrical impulse generator 310 for generation of the signal suitable for amelioration of the ailment when the signal is applied via the electrodes 340 to the device 100. It is noted that source 300 may be referred to by its function as a pulse generator.

Figure 4:
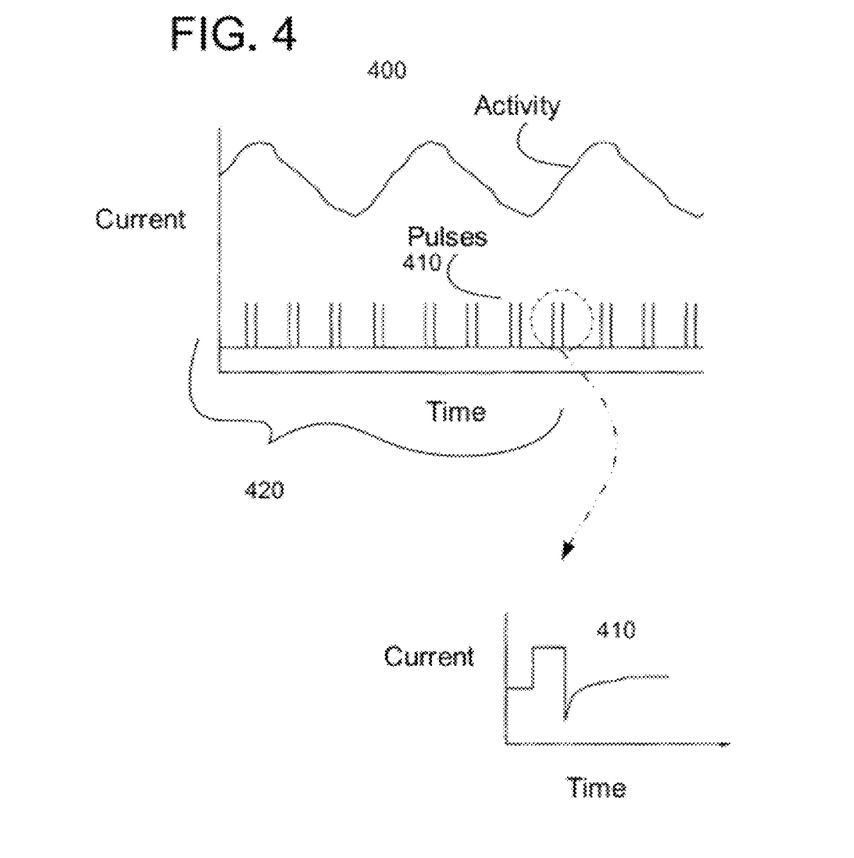
FIG. 4 illustrates an exemplary electrical voltage-current profile for a blocking and/or modulating impulse in accordance with an embodiment of the present invention.

FIG. 4 illustrates an exemplary electrical voltage/current profile for a blocking and/or modulating impulse applied to a portion or portions of the patient's anatomy, in accordance with one or more embodiments of the present invention. A suitable electrical voltage/current profile 400 for the blocking and/or modulating impulse 410 to the portion or portions of one or more nerves and/or muscles may be achieved using the pulse generator 310. In a preferred embodiment, the pulse generator 310 may be implemented using the power source 320 and control unit 330 having, for instance, a processor, a clock, a memory, etc., to produce a pulse train 420 to the electrode(s) 340 that deliver the blocking and/or modulating fields to the nerve resulting from impulses 410.

The parameters of the modulation signal 400 are preferably programmable, such as the frequency, amplitude, duty cycle, pulse width, pulse shape, etc. The blocking and/or modulating impulse signal 410 preferably has a frequency, an amplitude, a duty cycle, a pulse width, a pulse shape, etc. selected to influence the therapeutic result, such as blocking and/or modulating some or all of one or more nerve transmissions.

While the exact physiological causes of, for example, asthma and anaphylaxis have not been determined, the present invention postulates that the direct mediation of the smooth muscle constriction of the bronchia is the result of over-activity in the vagus nerve, which is a response to the flood of pro-inflammatory mediators interacting with the receptors on the nerve fibers themselves.

It has been observed in the literature that the nervous system maintains a balance of the signals carried by the sympathetic and parasympathetic nerves. The vagus nerve, as the source of the signal to constrict bronchial smooth muscle, is thought to provide a baseline level of tonicity in the smooth muscles surrounding the bronchial passages, in order to prevent the tissue lining the airways from collapsing shut.

Specifically, one or more embodiments of the present invention consider the signals carried by the vagus (parasympathetic) nerve to cause a constriction of the smooth muscle surrounding the bronchial passages. The sympathetic nerve fibers carry the opposing signals that tend to open the bronchial passages. It should be recognized that the signals of the vagus nerve mediate a response similar to that of histamine, while the sympathetic signals generate an effect similar to epinephrine. Given the postulated balance between the parasympathetic and sympathetic signals, removing the parasympathetic signal should create an imbalance emphasizing the sympathetic signal. Along these lines, scientific literature also indicates that severing the vagus nerve in dogs will open the bronchial passages, much the same way that epinephrine does.

In accordance with at least one aspect of the present invention, the delivery of an electromagnetic field sufficient to block and/or modulate transmission of signals in the vagus nerve will result in relaxation of the bronchi smooth muscle, dilating airways and/or counteracting the effect of histamine on the vagus nerve. Depending on the placement of the field, the signal blocking and/or modulation can also raise the heart function.

For example, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. For example, the at least one electrical signal may be of a frequency between about 15 Hz to 35 Hz, such as about 25 Hz. The at least one electrical signal may have a pulsed on-time of between about 50 to 1000 microseconds, such as between about 100 to 300 microseconds, such as about 200 microseconds. The at least one electrical signal may have an amplitude of about 5-15 volts, such as about 12 volts. The at least one electrical signal may include one or more of a full or partial sinusoid, a square wave, a rectangular wave, and triangle wave.

Although the specific implementation of the signal source 300 is not of criticality to the invention, by way of example, the source 300 may be purchased commercially, such as a Model 7432 available from Medtronic, Inc.

Alternatively, U.S. Patent Application Publications 2005/0075701 and 2005/0075702, both to Shafer, both of which are incorporated herein by reference, contain descriptions of pulse generators that may be applicable for implementing the signal source 300 of the present invention.

An alternative implementation for the signal source 300 of the present invention may be obtained from the disclosure of U.S. Patent Publication No. 2005/0216062, the entire disclosure of which is incorporated herein by reference. U.S. Patent Publication No. 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

A general approach to treating an ailment, such as bronchial constriction, hypotension, epilepsy, depression, obesity, and any other ailment affected by vagus nerve transmissions, etc., in accordance with one or more embodiments of the invention may include a method of (or apparatus for) treatment, comprising: inserting the balloon-electrode device 100 into an esophagus of the patient; inflating the balloon with fluid such that the electrode is substantially centrally located within an interior volume of the balloon; and applying at least one electrical signal to the electrode via the conductor such that an electromagnetic field emanates from the electrode to at least one nerve and/or muscle of the patient in the vicinity of the esophagus of the patient. The at least one electrical signal, in combination with electrical characteristics of the electrode, the fluid, and the material of the balloon, are such that at least one of: (i) a magnitude of constriction of bronchial smooth muscle of the mammal is reduced, (ii) the blood pressure of the mammal is either reduced or increased, (iii) incidents/magnitude of epilepsy episodes are reduced, (iv) depression is reduced, (v) obesity is reduced, and (vi) any other ailment affected by vagus nerve transmissions is improved.

The step of inserting the balloon-electrode device 100 and inflating the balloon 102 may include: inserting the balloon-electrode device 100 in a deflated state (but preferably primed) past a cricoid cartilage of the patient, inflating the balloon 102, and extracting the balloon 102 back toward the cricoid cartilage until it seats. Other approaches to positioning the balloon 102 may be used, such as using the hash marks discussed above.

Again, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. The polarity of the pulses may be maintained either positive or negative. Alternatively, the polarity of the pulses may be positive for some periods of the wave and negative for some other periods of the wave. By way of example, the polarity of the pulses may be altered from time to time or periodically.

Experiments were performed to identify exemplary methods of how the electromagnetic fields may be supplied to the patient to (i) reduce the sensitivity of the bronchial smooth muscle to the nerve signals to constrict, (ii) to blunt the intensity of, or break the constriction once it has been initiated.

Experimental pigs were pretreated with an intramuscular injection of 4.4 mg/kg Telazol and 2.2 mg/kg Xylazine, had venous access established in both ears for drug delivery, were intubated, and anesthetized with 1.5-3% isoflurane. The animals were maintained at 37° C. using a homeothermic heating pad placed on a ventilator (13-14 stroke/minute, 250-350 ml tidal volume, 35-45 mmHg $CO_2$, using Siemens equipment). A cannula was inserted into the left carotid artery to monitor blood pressure. After cannula insertion, the anesthesia was modified to use alpha chloralose (1 g/kg bolus and 1.5 g/hr infusion) and 0.3% isoflurane inhalation. The animals were ventilated through an endotracheal tube to provide positive pressure and constant volume ventilation. Pulmonary inflation pressure (ppi) and blood pressure were recorded and stored digitally (using pressure transducers and software by Biopac Systems Inc., Goleta, Calif.).

A balloon-electrode device 100 was inserted into the esophagus of the animals and positioned proximate to the nerves of interest (e.g., the vagus nerve). A conducting saline solution (5% NaCl) was introduced into the expanding balloon. The balloon was filled until it made contact with the inner wall of the esophagus (approximately a 1 cm radius). The wire attached to the electrode was then connected to a signal generator which delivered a square wave voltage pulse of 200 us duration, repeated at 25 Hz at voltages from 1 to 12 volts. The electrocaudery grounding plate, on the animal's back, or an EKG electrode placed on the animal's stomach, was used as the return electrode.

Figure 5A:
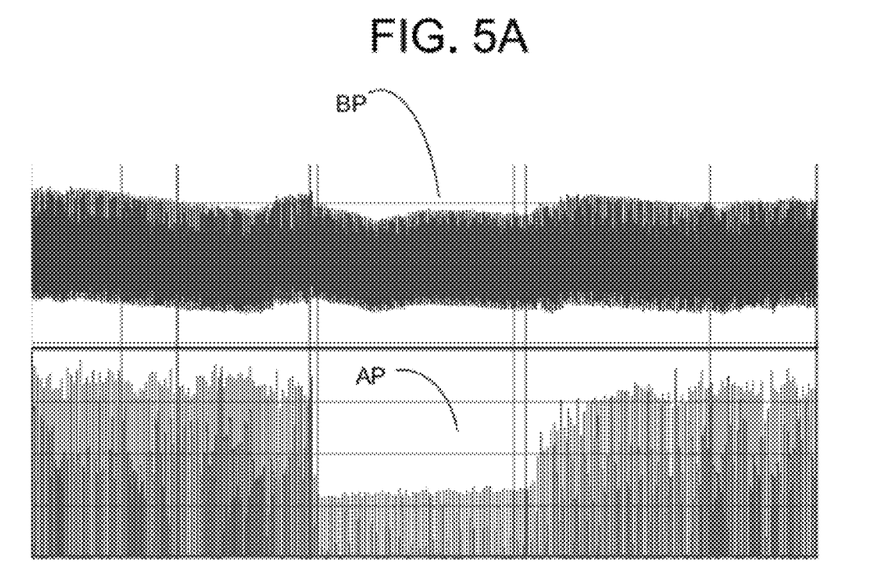
FIGS. 5A, 5B, 5C graphically illustrate exemplary experimental data obtained in accordance with multiple embodiments of the present invention.
Figure 5B:
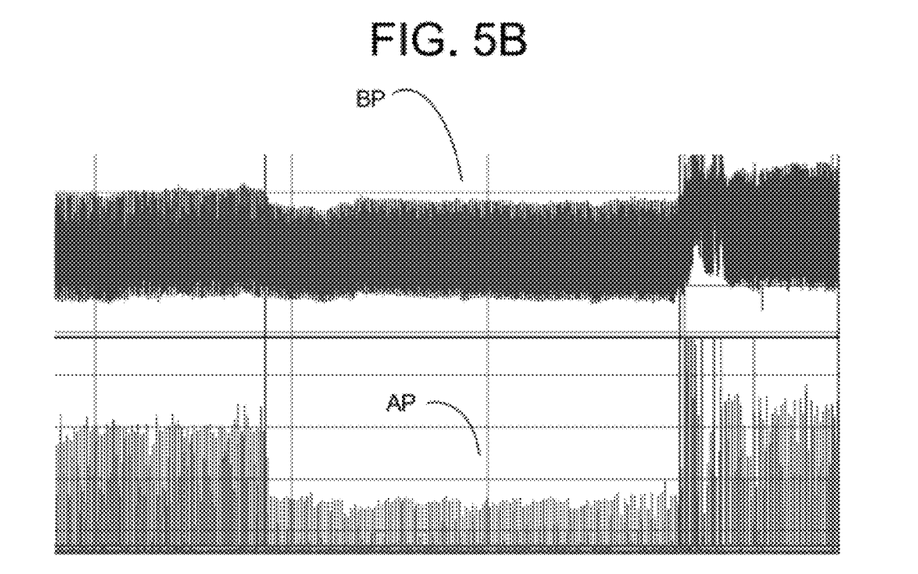
Figure 5C:
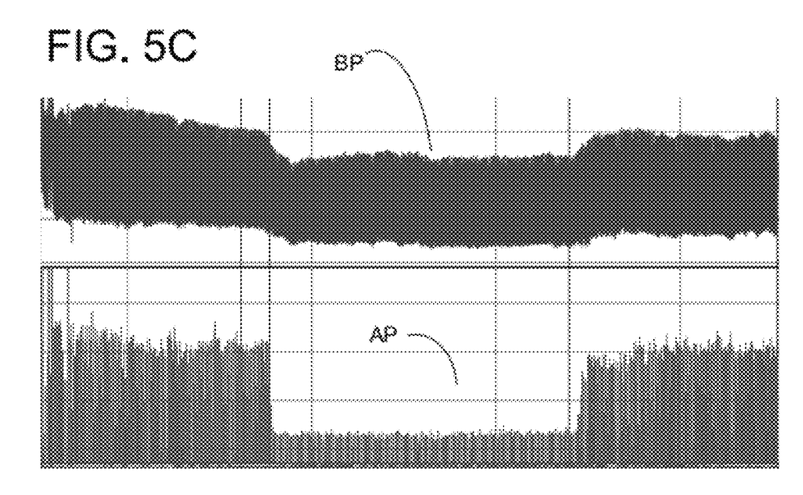

As shown in FIGS. 5A, 5B and 5C, electrical stimulation from within the esophagus caused rapid and significant drops in baseline airway resistance, along with corresponding drops in blood pressure. In all the graphs, the top line BP shows blood pressure, and the second line AP shows airway pressure. The electrical stimulation was maintained for up to 30 minutes (the maximum stimulation duration).

The esophageal electrode device 100 was also tested on one human patient to determine the safety of the procedure, ease of insertion, patient acceptability and effects of electrical stimulation. The esophageal electrode was inserted in one nostril and monitored continuously during insertion with a bronchoscope in the other nostril. No anesthesia was applied to the back of the throat but a standard lidocaine lubricant was placed on the ends of both the scope and the esophageal electrode before insertion. Insertion of the esophageal electrode through the nose and in to the throat took only a few seconds and was painless. When it reached the back of the throat, the patient was instructed to swallow repeatedly while the electrode was fed down the esophagus. There was a little irritation until the electrode was swallowed and then it was fairly comfortable. Next, about 6 cc of a room temperature 5% saline solution was injected in to the balloon. A cool sensation was felt in the throat but there was little discomfort and no gag reflex. The expanded balloon remained for several minutes. Swallowing was not hindered.

Blood pressure measurements were taken every few minutes with an automatic blood pressure cuff to monitor any changes in blood pressure. The generator was then turned on and voltage slowly increased. At about 8-10 volts a slight sensation was felt in the esophagus and under the TENS electrode (placed over the right pectoral muscle). The sensation was not unpleasant and the voltage was then turned up to its maximum, 12 V. Diastolic blood pressure increased from 90 to about 100 mm Hg during the procedure but may not have been related to the stimulation as the patient was somewhat nervous.

It was noted that when one attempted to pull the balloon up to the cricoid cartilage (the position of optimal response in the pig model), some resistance was felt. This information is believed to indicate a simple and precise positioning process: insert the balloon past the cricoid cartilage, inflate it, and then pull it back until it "seats" in the correct position.

To remove the electrode, fluid was sucked out of the balloon and the electrode was simply pulled from the esophagus and out through the nose. This process was painless and took just a few seconds.

A second balloon was inserted and the whole process repeated with similar results. Blood pressure remained elevated and did not increase with the second stimulation relative to its pre-stimulation level.

Figure 6:
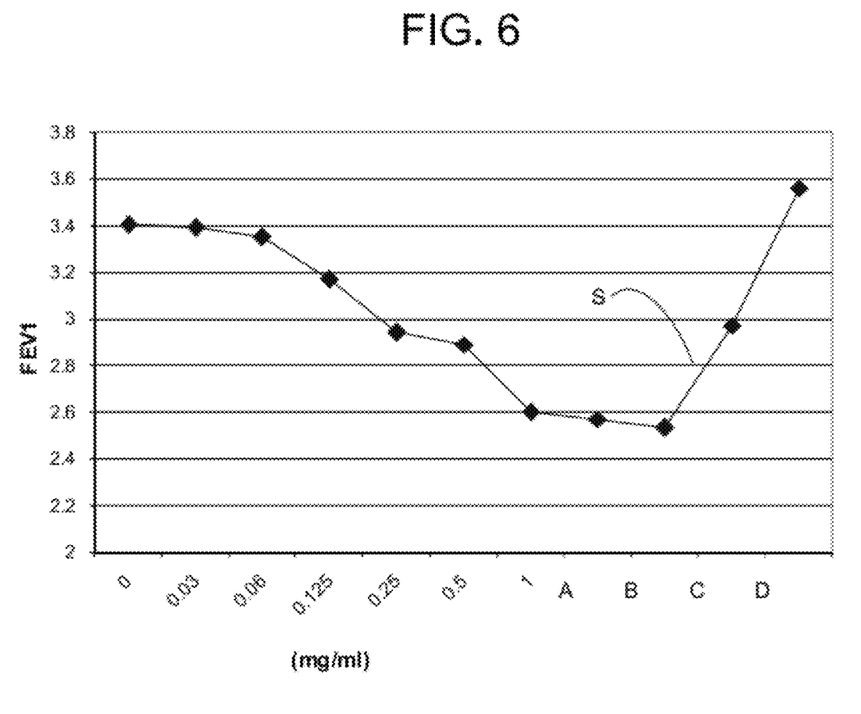
FIG. 6 graphically illustrates further experimental data obtained in accordance with embodiments of the present invention.

With reference to FIG. 6, in a further experiment on a human, increasing doses of methacholine were given to a patient until a drop of about 24% in forced expiratory volume (FEV) was observed at 1 mg/ml. (In the context of this application, forced expiratory volume is a measure of the of air during a forced vital capacity determination that can be expelled in a given number of seconds. A second FEV was taken (point A on the chart) prior to introducing the esophageal electrode device 100. The esophageal electrode device 100 was then inserted and another FEV was taken (point B). The stimulator was then turned on over interval S (from point C-D) to provide a signal having parameters consistent with those above, particularly with an amplitude of about 10 V for 4 minutes. The esophageal electrode device 100 was then removed and a post stimulation FEV was taken at point D, which shows a 16% increase. A final rescue albuterol treatment (post point D) restored the patient to normal FEV.

Figure 7A:
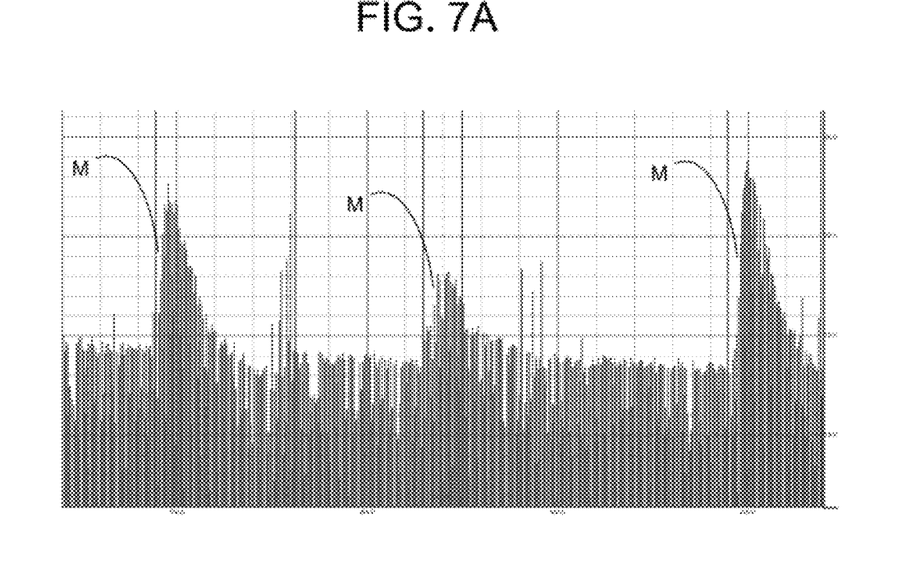
FIGS. 7A-7B graphically illustrate still further experimental data obtained in accordance with the present invention.
Figure 7B:
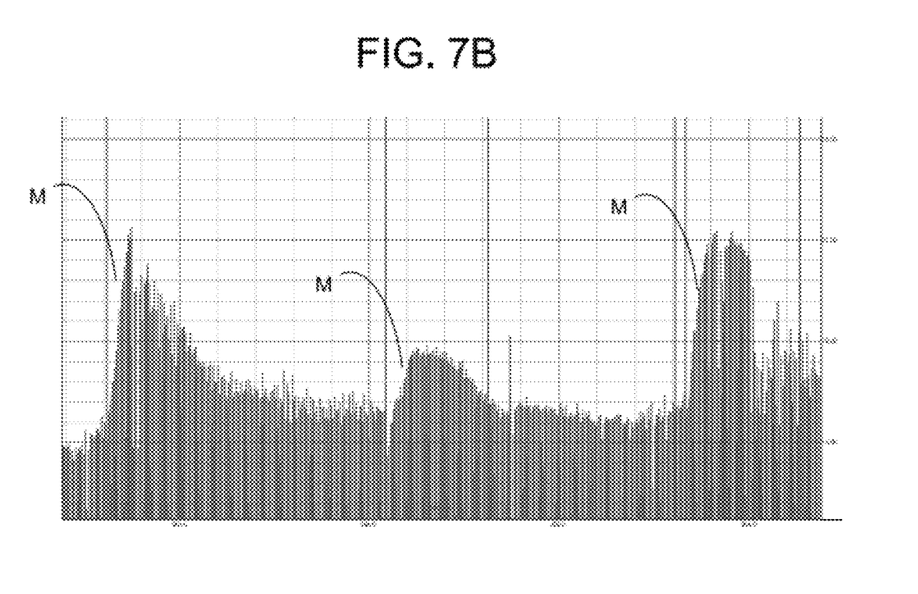

With reference to FIGS. 7A-7B, further experiments were conducted on pigs. In each of FIGS. 7A and 7B, airway pressure changes were measured in response to three methacholine challenges by nebulizer (indicated by the labels M). Each methacholine challenge was followed by an electrical stimulation through an esophageal electrode device 100 using signal parameters consistent with those discussed above. Two control traces bracket each challenge and stimulation. In the middle trace of each figure, electrical stimulation was applied just prior to turning on the nebulizer and remained on until just after the airway pressure peak. The stimulation using the esophageal electrode device 100 reduced the peak pressure increase by about 50%.

As discussed above, one or more embodiments of the present invention are directed to the delivery of electromagnetic fields to the anatomy of a mammal, such as to the vagus nerve and/or associated anatomy, using the device 100. In this regard, it has been discussed herein that a suitable location for the device 100 is within the esophagus of the patient such that radiating fields from the device 100 interact with the signals of one or more nerves, or muscles, to achieve a therapeutic result, such as relaxation of the smooth muscle of the bronchia, increase in blood pressure, reduction in blood pressure, treatment of epilepsy, depression, obesity, and/or any other ailment affected by vagus nerve transmissions, etc. In this regard, further details of the human anatomy are provide in connection with enabling a skilled artisan to determine further locations for the device 100 within the esophagus, signal parameters for driving the device 100, and/or further or different electrical characteristics of the device 100 to achieve therapeutic results.

The vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguus and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, vocalization and contraction of the facial muscles in relation to emotional states. Generally speaking, this portion of the vagus nerve regulates parasympathetic tone. The VVC inhibition is released (turned off) in states of alertness. This in turn causes cardiac vagal tone to decrease and airways to open, to support responses to environmental challenges.

The parasympathetic tone is balanced in part by sympathetic innervation, which generally speaking supplies signals tending to relax the bronchial muscles so over constriction does not occur. Overall, airway smooth muscle tone is dependent on several factors, including parasympathetic input, inhibitory influence of circulating epinephrine, NANC inhibitory nerves and sympathetic innervation of the parasympathetic ganglia. Stimulation of the vagus nerve (up-regulation of tone), such as occurs in asthma attacks or anaphylactic shock, results in airway constriction and a decrease in heart rate. In general, the pathology of both severe asthma and anaphylaxis appear to be mediated by inflammatory cytokines that overwhelm receptors on the nerve cells and cause the cells to massively up-regulate the parasympathetic tone.

In the case of asthma, it appears that the airway tissue has both (i) a hypersensitivity to the allergen that causes the overproduction of the cytokines that stimulate the cholinergic receptors of the nerves and/or (ii) a baseline high parasympathetic tone or a high ramp up to a strong parasympathetic tone when confronted with any level of cholinergic cytokine. The combination can be lethal. Anaphylaxis appears to be mediated predominantly by the hypersensitivity to an allergen causing the massive overproduction of cholinergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. As mentioned above, experience has shown that severing the vagus nerve (an extreme version of reducing the parasympathetic tone) has an effect similar to that of epinephrine and adrenaline on heart rate and bronchial diameter in that the heart begins to race (tachycardia) and the bronchial passageways dilate.

The sympathetic nerve fibers, along with many of the spinal cord's nerve root fibers, and the cranial nerves that innervate tissue in the thoracic and abdominal cavities are sometimes referred to as the autonomic, or vegetative, nervous system. The sympathetic, spinal, and cranial nerves all have couplings to the central nervous system, generally in the primitive regions of the brain, however, these components have direct effects over many regions of the brain, including the frontal cortex, thalamus, hypothalamus, hippocampus, and cerebellum. The central components of the spinal cord and the sympathetic nerve chain extend into the periphery of the autonomic nervous system from their cranial base to the coccyx, essentially passing down the entire spinal column, including the cervical, thoracic and lumbar regions. The sympathetic chain extends on the anterior of the column, while the spinal cord components pass through the spinal canal. The cranial nerves, the one most innervating of the rest of the body being the vagus nerve, passes through the dura mater into the neck, and then along the carotid and into the thoracic and abdominal cavities, generally following structures like the esophagus, the aorta, and the stomach wall.

Because the autonomic nervous system has both afferent and efferent components, modulation of its fibers can affect both the end organs (efferent) as well as the brain structure to which the afferents fibers are ultimately coupled within the brain.

Although sympathetic and cranial fibers (axons) transmit impulses producing a wide variety of differing effects, their component neurons are morphologically similar. They are smallish, ovoid, multipolar cells with myelinated axons and a variable number of dendrites. All the fibers form synapses in peripheral ganglia, and the unmyelinated axons of the ganglionic neurons convey impulses to the viscera, vessels and other structures innervated. Because of this arrangement, the axons of the autonomic nerve cells in the nuclei of the cranial nerves, in the thoracolumbar lateral comual cells, and in the gray matter of the sacral spinal segments are termed preganglionic sympathetic nerve fibers, while those of the ganglion cells are termed postganglionic sympathetic nerve fibers. These postganglionic sympathetic nerve fibers converge, in small nodes of nerve cells, called ganglia that lie alongside the vertebral bodies in the neck, chest, and abdomen. The effects of the ganglia as part of the autonomic system are extensive. Their effects range from the control of insulin production, cholesterol production, bile production, satiety, other digestive functions, blood pressure, vascular tone, heart rate, sweat, body heat, blood glucose levels, and sexual arousal.

The parasympathetic group lies predominately in the cranial and cervical region, while the sympathetic group lies predominantly in the lower cervical, and thoracolumbar and sacral regions. The sympathetic peripheral nervous system is comprised of the sympathetic ganglia that are ovoid/bulb like structures (bulbs) and the paravertebral sympathetic chain (cord that connects the bulbs). The sympathetic ganglia include the central ganglia and the collateral ganglia.

The central ganglia are located in the cervical portion, the thoracic portion, the lumbar portion, and the sacral portion. The cervical portion of the sympathetic system includes the superior cervical ganglion, the middle cervical ganglion, and the interior cervical ganglion.

The thoracic portion of the sympathetic system includes twelve ganglia, five upper ganglia and seven lower ganglia. The seven lower ganglia distribute filaments to the aorta, and unite to form the greater, the lesser, and the lowest splanchnic nerves. The greater splanchnic nerve (splanchnicus major) is formed by branches from the fifth to the ninth or tenth thoracic ganglia, but the fibers in the higher roots may be traced upward in the sympathetic trunk as far as the first or second thoracic ganglion. The greater splanchnic nerve descends on the bodies of the vertebrae, perforates the crus of the diaphragm, and ends in the celiac ganglion of the celiac plexus. The lesser splanchnic nerve (splanchnicus minor) is formed by filaments from the ninth and tenth, and sometimes the eleventh thoracic ganglia, and from the cord between them. The lesser splanchnic nerve pierces the diaphragm with the preceding nerve, and joins the aorticorenal ganglion. The lowest splanchnic nerve (splanchnicus imus) arises from the last thoracic ganglion, and, piercing the diaphragm, ends in the renal plexus.

The lumbar portion of the sympathetic system usually includes four lumbar ganglia, connected together by interganglionic cords. The lumbar portion is continuous above, with the thoracic portion beneath the medial lumbocostal arch, and below with the pelvic portion behind the common iliac artery. Gray rami communicantes pass from all the ganglia to the lumbar spinal nerves. The first and second, and sometimes the third, lumbar nerves send white rami communicantes to the corresponding ganglia.

The sacral portion of the sympathetic system is situated in front of the sacrum, medial to the anterior sacral foramina. The sacral portion includes four or five small sacral ganglia, connected together by interganglionic cords, and continuous above with the abdominal portion. Below, the two pelvic sympathetic trunks converge, and end on the front of the coccyx in a small ganglion.

The collateral ganglia include the three great gangliated plexuses, called, the cardiac, the celiac (solar or epigastric), and the hypogastric plexuses. The great plexuses are respectively situated in front of the vertebral column in the thoracic, abdominal, and pelvic regions. They consist of collections of nerves and ganglia; the nerves being derived from the sympathetic trunks and from the cerebrospinal nerves. They distribute branches to the viscera.

The celiac plexus is the largest of the three great sympathetic plexuses and is located at the upper part of the first lumbar vertebra. The celiac plexus is composed of the celiac ganglia and a network of nerve fibers uniting them together. The celiac plexus and the ganglia receive the greater and lesser splanchnic nerves of both sides and some filaments from the right vagus nerve. The celiac plexus gives off numerous secondary plexuses along the neighboring arteries. The upper part of each celiac ganglion is joined by the greater splanchnic nerve, while the lower part, which is segmented off and named the aorticorenal ganglion, receives the lesser splanchnic nerve and gives off the greater part of the renal plexus.

The secondary plexuses associated with the celiac plexus consist of the phrenic, hepatic, lineal, superior gastric, suprarenal, renal, spermatic, superior mesenteric, abdominal aortic, and inferior mesenteric. The phrenic plexus emanates from the upper part of the celiac ganglion and accompanies the inferior phrenic artery to the diaphragm, with some filaments passing to the suprarenal gland and branches going to the inferior vena cava, and the suprarenal and hepatic plexuses. The hepatic plexus emanates from the celiac plexus and receives filaments from the left vagus and right phrenic nerves. The hepatic plexus accompanies the hepatic artery and ramifies upon its branches those of the portal vein in the substance of the liver. Branches from hepatic plexus accompany the hepatic artery, the gastroduodenal artery, and the right gastroepiploic artery along the greater curvature of the stomach.

The lienal plexus is formed from the celiac plexus, the left celiac ganglion, and from the right vagus nerve. The lienal plexus accompanies the lienal artery to the spleen, giving off subsidiary plexuses along the various branches of the artery. The superior gastric plexus accompanies the left gastric artery along the lesser curvature of the stomach, and joins with branches from the left vagus nerve. The suprarenal plexus is formed from the celiac plexus, from the celiac ganglion, and from the phrenic and greater splanchnic nerves. The suprarenal plexus supplies the suprarenal gland. The renal plexus is formed from the celiac plexus, the aorticorenal ganglion, and the aortic plexus, and is joined by the smallest splanchnic nerve. The nerves from the suprarenal plexus accompany the branches of the renal artery into the kidney, the spermatic plexus, and the inferior vena cava.

The spermatic plexus is formed from the renal plexus and aortic plexus. The spermatic plexus accompanies the internal spermatic artery to the testis (in the male) and the ovarian plexus, the ovary, and the uterus (in the female). The superior mesenteric plexus is formed from the lower part of the celiac plexus and receives branches from the right vagus nerve.

The superior mesenteric plexus surrounds the superior mesenteric artery and accompanies it into the mesentery, the pancreas, the small intestine, and the great intestine. The abdominal aortic plexus is formed from the celiac plexus and ganglia, and the lumbar ganglia. The abdominal aortic plexus is situated upon the sides and front of the aorta, between the origins of the superior and inferior mesenteric arteries, and distributes filaments to the inferior vena cava. The inferior mesenteric plexus is formed from the aortic plexus. The inferior mesenteric plexus surrounds the inferior mesenteric artery, the descending and sigmoid parts of the colon and the rectum.

While the sympathetic and parasympathetic nervous system extends between the brain and the great plexuses, the cranial nerves extend between the brain and the great plexuses along other paths.

There are twelve pairs of cranial nerves, namely: the olfactory, optic, oculomotor, trochlear, trigeminal, abducent, facial, acoustic, glossopharyngeal, vagus, accessory, and hypoglossal. The nuclei of origin of the motor nerves and the nuclei of termination of the sensory nerves are brought into relationship with the cerebral cortex.

Although all of the cranial nerves are of interest in accordance with various embodiments of the present invention, by way of example, the vagus nerve may be of particular interest. The vagus nerve is composed of motor and sensory fibers and is of considerable interest in connection with various embodiments of the present invention because it has a relatively extensive distribution than the other cranial nerves and passes through the neck and thorax to the abdomen. The vagus nerves leaves the cranium and is contained in the same sheath of dura mater with the accessory nerve. The vagus nerve passes down the neck within the carotid sheath to the root of the neck. On the right side, the nerve descends by the trachea to the back of the root of the lung, where it spreads out in the posterior pulmonary plexus. From the posterior pulmonary plexus, two cords descend on the esophagus and divide to form the esophageal plexus. The branches combine into a single cord, which runs along the back of the esophagus, enters the abdomen, and is distributed to the posteroinferior surface of the stomach, joining the left side of the celiac plexus, and sending filaments to the lienal plexus.

On the left side, the vagus nerve enters the thorax, crosses the left side of the arch of the aorta, and descends behind the root of the left lung, forming the posterior pulmonary plexus. From posterior pulmonary plexus, the vagus nerve extends along the esophagus, to the esophageal plexus, and then to the stomach. The vagus nerve branches over the anterosuperior surface of the stomach, the fundus, and the lesser curvature of the stomach.

The branches of distribution of the vagus nerve are as follows: the auricular, the superior laryngeal, the recurrent, the superior cardiac, the inferior cardiac, the anterior bronchial, the posterior bronchial, the esophageal, the celiac, and the hepatic. The gastric branches are distributed to the stomach, where the right vagus nerve forms the posterior gastric plexus on the postero-inferior surface of the stomach and the left vagus nerve forms the anterior gastric plexus on the antero-superior surface of the stomach. The celiac branches are mainly derived from the right vagus nerve, which enter the celiac plexus and supply branches to the pancreas, spleen, kidneys, suprarenal bodies, and intestine.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for delivering an electromagnetic field to a mammal, comprising:
   a nasogastral (NG) tube having an internal passageway and an external surface;
   at least one electrode coupled to the external surface of the NG tube;
   a conductor extending through the internal passageway of the NG tube and electrically coupled to the electrode; and
   a balloon surrounding the electrode and a portion of the NG tube such that when the balloon is inflated with fluid, the electrode is substantially centrally located within an interior volume of the balloon.

2. The device of claim 1, wherein the at least one electrode is generally cylindrically-shaped and extends around the external surface of the NG tube.

3. The device of claim 2, wherein at least one of: (i) the at least one electrode is between about 1.0-1.5 mm long; (ii) an outside diameter of the at least one electrode is between about 2.6-2.85 mm; and an inside diameter of the at least one electrode is between about 2.5-2.75 mm.

4. The device of claim 1, wherein the NG tube includes a first aperture through which the conductor passes from the internal passageway to the at least one electrode.

5. The device of claim 4, wherein the NG tube includes at least one of second and third apertures extending from the internal passageway to the external surface, and through which the fluid may pass to inflate and deflate the balloon.

6. The device of claim 5, wherein the second and third apertures are disposed at proximal and distal ends of the balloon, respectively, and the first aperture is located between the second and third apertures.

7. The device of claim 1, wherein the balloon is formed from an ion-permeable material.

8. The device of claim 1, wherein at least one of: (i) a length of the balloon is between about 1-3 cm; (ii) a diameter of the balloon when inflated is between about 1.5-4.0 cm; and (iii) a fluid pressure within the balloon is between about 1-3 pounds per square inch when inflated.

9. The device of claim 1, wherein electrical properties of the electrode, the fluid, and the material of the balloon are such that a resistance through the electrode, the fluid, and the material of the balloon is no more than about 200 Ohms.

10. The device of claim 9, wherein the fluid is about 5% saline solution.

11. The device of claim 1, further comprising an electrical signal generator operating to apply at least one electrical signal to the conductor such that, when the inflated balloon and electrode combination is positioned in an esophagus of the mammal, an electro-magnetic field emanates from the electrode to at least one of nerves and muscles in a vicinity of the esophagus of the mammal.

12. The device of claim 1, wherein at least one of:
the electro-magnetic field emanates from the electrode to at least a vagus nerve of the mammal; and
the at least one electrical signal, in combination with electrical characteristics of the electrode, the fluid, and the material of the balloon, are such that at least one of: (i) a magnitude of constriction of bronchial smooth muscle of the mammal is reduced, (ii) a blood pressure of the mammal is either reduced or increased, (iii) epilepsy, (iv) depression, (v) obesity, and (vi) any other ailment affected by vagus nerve transmissions.

13. The device of claim 11, further comprising a return electrode, which when applied to the mammal, the electromagnetic field emanating from the electrode is a substantially radial pattern.

14. The device of claim 11, wherein the balloon is sized and shaped such that it operates to: (i) slide, in a deflated state, past a cricoid cartilage of the mammal, and (ii) seat, when in an inflated state, when slid back toward the cricoid cartilage.

15. The device of claim 11, wherein at least one of:
electrical properties of the electrode, the fluid, and the material of the balloon are such that a resistance through the electrode, the fluid, and the material of the balloon is no more than about 200 Ohms; and
the electrical signal generator operates such that the at least one electrical signal is of a frequency between about 1 Hz to 3000 Hz, a pulse duration of between about 10-1000 us, and an amplitude of between about 1-20 volts.

16. The device of claim 15, wherein the at least one electrical signal is of a frequency between about 15 Hz to 35 Hz.

17. The device of claim 16, wherein the at least one electrical signal is of a frequency of about 25 Hz.

18. The device of claim 15, wherein the at least one electrical signal has a pulsed on-time of between about 50 to 1000 microseconds.

19. The device of claim 18, wherein the at least one electrical signal has a pulsed on-time of between about 100 to 300 microseconds.

20. The device of claim 18, wherein the at least one electrical signal has a pulsed on-time of about 200 microseconds.

21. The device of claim 15, wherein the at least one electrical signal has an amplitude of about 5-15 volts.

22. The device of claim 15, wherein the at least one electrical signal has an amplitude of about 12 volts.

23. The device of claim 15, wherein the at least one electrical signal is one or more of a full or partial sinusoid, a square wave, a rectangular wave, and triangle wave.

24. A device for delivering an electro-magnetic field to a mammal, comprising:
a nasogastral (NG) tube having an internal passageway and an external surface; and
a balloon surrounding a portion of the NG tube such that when the balloon is inflated with conductive fluid, the fluid acts as an electrode within an interior volume of the balloon.

25. The device of claim 24, further comprising a conductive fluid extending through the internal passageway of the NG tube to provide a path for electrical current to flow to the fluid within the balloon.

26. The device of claim 24, further comprising a conductor extending through the internal passageway of the NG tube to provide a path for electrical current to flow to the fluid within the balloon.

27. A method of treating an ailment, comprising:
inserting a balloon-electrode device into an esophagus of a mammal, the balloon-electrode device including:
a nasogastral (NG) having an internal passageway and an external surface,
at least one electrode coupled to the external surface of the NG tube,
a conductor extending through the internal passageway of the NG tube and electrically connecting to the electrode, and
a balloon surrounding the electrode and a portion of the NG tube;
inflating the balloon with fluid such that the electrode is substantially centrally located within an interior volume of the balloon; and
applying at least one electrical signal to the electrode via the conductor such that an electro-magnetic field emanates from the electrode to at least one of nerves and muscles the mammal.

28. The method of claim 27, wherein at least one of:
applying the least one electrical signal to the electrode via the conductor results in an electro-magnetic field emanating from the electrode to at least a vagus nerve of the mammal; and
the at least one electrical signal, in combination with electrical characteristics of the electrode, the fluid, and the material of the balloon, are such that at least one of: (i) a magnitude of constriction of bronchial smooth muscle of the mammal is reduced, (ii) a blood pressure of the mammal is either reduced or increased, (iii) epilepsy, (iv) depression, (v) obesity, and (vi) any other ailment affected by vagus nerve transmissions.

29. The method of claim 27, further comprising applying a return electrode to the mammal such that the electro-magnetic field emanating from the electrode is a substantially radial pattern.

30. The method of claim 27, further comprising applying a return electrode to an external portion of the mammal.

31. The method of claim 30, wherein the external portion of the mammal is at least one of the mammal's upper-back, the mammal's chest, and the mammal's stomach.

32. The method of claim 27, wherein the step of inserting the balloon-electrode device and inflating the balloon includes: inserting the balloon-electrode device in a deflated state past a cricoid cartilage of the mammal, inflating the balloon, and extracting the balloon-electrode device back toward the cricoid cartilage until it seats.

33. The method of claim 27, wherein at least one of:
electrical properties of the electrode, the fluid, and the material of the balloon are such that a resistance through the electrode, the fluid, and the material of the balloon is no more than about 200 Ohms; and
the at least one electrical signal is of a frequency between about 1 Hz to 3000 Hz, a pulse duration of between about 10-1000 us, and an amplitude of between about 1-20 volts.

34. The method of claim 33, wherein the at least one electrical signal is of a frequency between about 15 Hz to 35 Hz.

35. The method of claim 34, wherein the at least one electrical signal is of a frequency of about 25 Hz.

36. The method of claim 33, wherein the at least one electrical signal has a pulsed on-time of between about 50 to 1000 microseconds.

37. The method of claim 36, wherein the at least one electrical signal has a pulsed on-time of between about 100 to 300 microseconds.

38. The method of claim 36, wherein the at least one electrical signal has a pulsed on-time of about 200 microseconds.

39. The method of claim 33, wherein the at least one electrical signal has an amplitude of about 5-15 volts.

40. The method of claim 33, wherein the at least one electrical signal has an amplitude of about 12 volts.

41. The method of claim 33, wherein the at least one electrical signal is one or more of a full or partial sinusoid, a square wave, a rectangular wave, and triangle wave.

* * * * *